(12) United States Patent
Love

(10) Patent No.: US 6,221,622 B1
(45) Date of Patent: *Apr. 24, 2001

(54) METHOD AND KIT FOR OBTAINING FLUIDS AND CELLULAR MATERIAL FROM BREAST DUCTS

(75) Inventor: Susan M. Love, Pacific Palisades, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/067,661

(22) Filed: Apr. 28, 1998

(51) Int. Cl.$^7$ .................. G01N 33/574; G01N 33/561; A61M 1/00; A61M 29/00

(52) U.S. Cl. .................. 435/7.23; 435/7.21; 604/28; 604/30; 604/35; 604/104; 119/14.19

(58) Field of Search .................. 435/7.1, 7.23; 604/28, 30, 35, 104; 119/14.19

(56) References Cited

U.S. PATENT DOCUMENTS 5,413,558 * 5/1995 Paradis .

FOREIGN PATENT DOCUMENTS

WO 97/05898   2/1997   (WO).
WO99/13917    3/1999   (WO).

OTHER PUBLICATIONS

Barsky et al., "Pathologic analysis of breast duct endoscoped mastectomies" *Laboratory Investigation, Modern Pathology*, Annual Meeting Abstracts (1996) p. 15A, abstract No. 67.

Fabian et al., "Prevalence of abnormal biomarkers in fine needle breast aspirates in a high risk population: Potential for use in risk prediction" *Proc. Ann. Meet. Am. Assoc. Cancer Res.* (1993) 34:A1556.

Imayama et al., "Presence of elevated carcinoembryonic antigen on absorbent disks applied to nipple area of breast carcinoma patients" *Cancer* (1996) 78(6) :1229–1234.

Lewis, "Technique probes breast ducts for cancer cells" *Biophotonics International* (May/Jun. 1997) pp. 27–28.

Love, "Breast duct endoscopy: A pilot study of a potential technique for evaluating intraductal disease" 15th Annual San Antonio Breast Cancer Symposium, San Antonio, TX (1996) p. 180, abstract No. 197.

Love and Barsky, "Breast–duct endoscopy to study stages of cancerous breast disease" *The Lancet* (1996) 348:997–999.

Makita et al., "Duct endoscopy and endoscopic biopsy in the evaluation of nipple discharge" *Breast Cancer Research and Treatment* (1991) 18:179–187.

Okazaki et al., "Fiberoptic ductoscopy of the breast: A new diagnostic procedure for nipple discharge" *Jpn. J. Clin. Oncol.* (1991) 21(3):188–193.

(List continued on next page.)

Primary Examiner—Julie Burke
Assistant Examiner—Lin Sun-Hoffman
(74) Attorney, Agent, or Firm—Gates & Cooper (57) ABSTRACT

Methods, kits, and apparatus for obtaining cellular, chemical, and other materials from breast ducts are described. A single milk duct is accessed and washed with a washing fluid to obtain marker materials from the lining the duct. The washing fluid is then collected, and the marker materials in the washing fluid identified and analyzed. Usually, the washing fluid is introduced using a syringe through a lumen of a dual-lumen catheter. The ductal volume is filled with the washing fluid and excess fluid flows outwardly through a second lumen of the dual-lumen catheter, from which it is collected.

33 Claims, 6 Drawing Sheets

OTHER PUBLICATIONS

Petrakis, "Physiologic, biochemical, and cytologic aspects of nipple aspirate fluid" *Breast Cancer Research and Treatment* (1986) 8:7–19.

Petrakis, "Studies on the epidemiology and natural history of benign breast disease and breast cancer using nipple aspirate fluid" *Cancer Epidemiology, Biomarkers & Prevention* (Jan./Feb. 1993) 2:3–10.

Petrakis, "Nipple aspirate fluid in epidemiologic studies of breast disease" *Epidemiologic Reviews* (1993) 15:188–195.

Sartorius et al., "Contrast ductography for recognition and localization of benign and malignant breast lesions: An improved technique" Logan, W., ed., *Breast Carcinoma*, New York, Wiley, (1977) pp. 281–300.

Sartorius, "The biochemistry of breast cyst fluids and duct secretions" Breast *Cancer Research and Treatment* (1995) 35:255–266.

Wrensch et al., "Breast fluid cholesterol and cholesterol β–epoxide concentrations in women with benign breast disease" *Cancer Res.* (1989) 49:2168–2174.

Wrensch et al., "Factors associated with obtaining nipple aspirate fluid: Analysis of 1428 women and literature review" *Breast Cancer Research and Treatment* (1990) 15:39–51.

Wrensch et al., "Breast cancer incidence in women with abnormal cytology in nipple aspirates of breast fluid" *Am. J. Epidemiol.* (1992) 135(2):130–141.

Love et al., The Lancet. 348:997–999, 1996.*

Akira Okazaki, "Diagnosis of Nonpalpable Breast Cancer By Ductoscopy: Comparison of Imaging and Histological Findings", Nyugan no Rinsho (Clinical Breast Cancer) 4(4):587–594 (1989).

Claude Feige, "Dynamic Morpho–Cyto–Echography and the Echographic Galactoscopy Endo–Ductal Sample Intrinsic and Extrinsic Markers in the Detection of Breast Cancers", *Ultrasound in Med. & Biol.,* vol. 14, Sup. 1, pp. 97–108, 1982.

Jeffrey A. Fisher, "Our Medical Future: Breathroughs in Health and Longevity by the Year 2000 and Beyond", Copyright 1992, book published by Pocket Books, New York, NY, U.S.A., pp. 136–141.

Raul A. Leborgne, "The Breast in Roentgen Diagnosis", Impressora Uruguaya S.A.—Juncal[51], Montevideo (Uruguay), 1953.

Carol J. Fabian et al., "Biomarker and Cytologic Abnormalities in Women at High and Low Risk for Breast Cancer", Journal of Cellular Biochemistry, 17G:153–160 (1993).

M. Falardeau et al., "Selective Galactophorectomy for Mono–Orificial Nipple Discharge Without Associated Mass: Technique and Results. Apropos of seventy–three cases", Database Medline 'Online', US National Library of Medicine, Bethesda, Maryland, USA, (Abstract) and [Annales De Chirurgie, (1991) 45(9)796–801, Journal code: 50E. ISSN: 0003–3944].

C. Feige, "Dynamic Morpho–cyto–echography and the Echographic Galactoscopy Endo–ductal sample. Intrinsic and Extrinsic Markers in the Detection of Breast Cancers", Database Medline 'Online', US National Library of Medicine, Bethesda, Maryland, USA, (Abstract) AN=8904507 and ["Ultrasound in Medicine and Biology", (1998) 14 Suppl 1 97–108. Journal Code: WNE.ISSN: 0301–5629, United Kingdom.].

M. F. Hou et al., "A Simple Method of Duct Cannulation and Localization for Galactography Before Excision in Patients with Nipple Discharge", Radiology, (May 1995), 195(2) 568–9, Journal Code: QSH.ISSN: 0033–8419., XP002091599, United States.

Tomoaki Katamine et al., "Determination of Cancer–associated Antigens in Body Fluid Secreted from Nipple" Chemical Abstracts, vol. 114, No. 9, Mar. 4, 1991, 2pp, and JP 02 280061 A (Mochida Pharmaceutical Co., Ltd., Japan).

S. Naran et al., "Cytologic Diagnosis of Papillary Carcinoma of the Breast in Needle Aspirates", Database Medline Online, US National Library of Medicine, Bethesda, Maryland, US, an=88242405, Database Accession No. 88242405 XP002114398 (Abstract) and [Diagnostic Cytopathology, (Mar. 1988) 4(1) 33–7.].

F. A. Weaver et al., "Management of Postoperative Lymphatic Leaks by Use of Isosulphan Blue '3!", Database EMBASE 'Online', Elsevier Science Publishers, Amsterdam, Netherlands, Database Accession No. 91353868, XP002114397 (Abstract) and [Journal of Vascular Surgery, (1991) 14/4 (566–567).].

Margaret Wrensch, et al., "Breast Cancer Risk Associated with Abnormal Cytology in Nipple Aspirates of Breast Fluid and Prior History of Breast Biopsy", American Journal of Epidemiology, vol. 137, No. 8, 1993, pp. 829–833.

Akira Okazaki et al., "Relationship Between Cytologic Results and the Extent of Intraductal Spread in Nonpalpable Breast Cancers with Nipple Discharge", *Tumor Res.,* 31, pp. 89–97, 1996.

* cited by examiner

METHOD AND KIT FOR OBTAINING FLUIDS AND CELLULAR MATERIAL FROM BREAST DUCTS

This invention was made with Government support under contract DAMD17-96-C-6117. The government has certain rights in this invention.

BACKGROUND OF THE INVENTION

1. Field of the Invention

The present invention relates generally to medical methods and apparatus for obtaining fluids and cellular materials from a patient. More particularly, the present invention relates to methods and apparatus for obtaining epithelial cells from the lining of a breast milk duct.

Breast cancer is the most common cancer in women, with well over 100,000 new cases being diagnosed each year. Even greater numbers of women, however, have symptoms associated with breast diseases, both benign and malignant, and must undergo further diagnosis and evaluation in order to determine whether breast cancer exists. To that end, a variety of diagnostic techniques have been developed, the most common of which are surgical techniques including core biopsy and excisional biopsy. Recently, fine needle aspiration (FNA) cytology has been developed which is less invasive than the surgical techniques, but which is not always a substitute for surgical biopsy.

A variety of other diagnostic techniques have been proposed for research purposes. Of particular interest to the present invention, fluids from the breast ducts have been externally collected, analyzed, and correlated to some extent with the risk of breast cancer. Such fluid collection, however, is generally taken from the surface of the nipple and includes material from all of the ductal structures. Information on the condition of an individual duct is generally not provided. Information on individual ducts can be obtained through cannulation and endoscopic or fluoroscopic examination, but such examinations have been primarily in women with nipple discharge or for research purposes and have generally not examined each individual duct in the breast.

Since breast cancer usually arises from a single ductal system and exists in a precancerous state for a number of years, endoscopy in and fluid collection from individual breast ducts holds great diagnostic promise for the identification of intermediate markers. Of particular interest to the present invention, it would be of great value to be able to reliably collect ductal fluids and cellular and non-cellular marker materials (e.g. epithelial and other cells as well as proteins, carbohydrates, and other non-cellular marker materials) from the individual breast ducts on a duct-by-duct basis. By examining the collected marker materials, cancerous and pre-cancerous conditions within each duct could be identified at a very early stage. Moreover, by associating the condition with a specific duct, treatment could be directed specifically at that duct in an attempt to enhance the effectiveness of the treatment and minimize trauma to the patient.

The ability to perform such diagnostic techniques, however, has been limited. Heretofore, it has been very difficult to identify ductal orifices in a reliable and consistent manner. That problem, however, has been addressed by the invention reported in co-pending, commonly assigned application Ser. No. 08/931,786, filed on Sep. 16, 1997, the full disclosure of which is incorporated herein by reference. By labeling the ductal orifices, the location of the entry orifice for each duct can be established.

Even though access to all of the ducts in a breast can now be achieved, successful diagnostic methods will depend on the ability to collect cellular and non-cellular materials from at least, most, and preferably all, regions of each ductal network. Breast ducts have highly complex and convoluted three-dimensional geometries, with more remote portions of the network having increasingly smaller diameters. Thus, obtaining representative material samples from throughout a ductal network represents a significant challenge.

Prior attempts to obtain cellular material from individual breast ducts have been only partly successful. As reported by the inventor herein, in Love and Barsky (1996) *The Lancet* 348:997–999, breast ducts have been cannulated with a rigid cannula and instilled with very small volumes (0.2 ml to 0.5 ml) of saline. Saline was recovered separately through a capillary tube, and cellular material recovered from the saline. It was not clear, however, if cellular material was recovered from most or all portions of the ductal network. Unless such representative samples can be obtained, reliable diagnostics cannot be performed. While the paper proposes development of a two-lumen catheter, no such catheter or its use is described in the publication.

For these reasons, to enable the performance of ductal diagnostic techniques, it will be useful to provide methods and apparatus which permit the collection of fluids and marker materials from individual ductal networks in a reliable and consistent fashion. Such methods should be minimally traumatic to the patient, should be useful for routine screening in at least high-risk patients, and should provide cellular and non-cellular materials suitable for reliable detection of cancerous and pre-cancerous conditions. At least some of these objectives will be met by the invention described hereinafter.

2. Description of the Background Art

Publications by the inventor herein relating to breast duct access include Love and Barsky (1996) Lancet 348: 997–999; Love (1992) "Breast duct endoscopy: a pilot study of a potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modern Pathology, Abstract 67. A description of the inventor's earlier breast duct access work was presented in Lewis (1997) Biophotonics International, pages 27–28, May/June 1997.

Nipple aspiration and/or the introduction of contrast medium into breast ducts prior to imaging are described in Sartorius (1995) Breast Cancer Res. Treat. 35: 255–266; Satorious et al. (1977) "Contrast ductography for the recognition and localization of benign and malignant breast lesions: An improved technique," in: Logan (ed.), Breast Carcinoma, New York, Wiley, pp. 281–300; Petrakis (1993) Cancer Epidem. Biomarker Prev. 2: 3–10; Petrakis (1993) Epidem. Rev. 15: 188–195; Petrakis (1986) Breast Cancer Res. Treat. 8: 7–19; Wrensch et al. (1992) Am. J. Epidem. 135: 130–141; Wrensch et al. (1990) Breast Cancer Res. Treat. 15: 39–51; and Wrensch et al. (1989) Cancer Res. 49: 2168–2174. The presence of abnormal biomarkers in fine needle breast aspirates is described in Fabian et al. (1993) Proc. Ann. Meet. Am. Assoc. Cancer Res. 34: A1556. The use of a rigid 1.2 mm ductoscope to identify intraductal papillomas in women with nipple discharge is described in Makita et al. (1991) Breast Cancer Res. Treat. 18: 179–188. The use of a 0.4 mm flexible scope to investigate nipple discharge is described in Okazaki et al. (1991) Jpn. J. Clin. Oncol. 21: 188–193. The detection of CEA in fluids obtained by a nipple blot is described in Imayama et al. (1996) Cancer 78: 1229–1234. Delivery of epithelium-destroying agents to breasts by ductal cannulation is described in WO 97/05898.

SUMMARY OF THE INVENTION

The present invention provides improved methods, kits, and other apparatus for obtaining fluids, marker substances, cellular material, and the like (referred to hereinafter as "marker materials") from single milk ducts in the breasts of human female patients. In particular, the methods of the present invention permit reliable washing and retrieval of marker materials from an entire network of a single milk duct to enable screening, diagnosis, and monitoring of diseases associated with the lining of the milk duct, particularly for identifying cancer and pre-cancerous conditions. As the marker materials are obtained entirely from a single ductal network, diagnosis can be made on a duct-by-duct basis. By obtaining specimens from each one of the multiple ductal networks in a breast, however, the presence of disease or increased likelihood of disease in the entire breast can also be determined.

In a first aspect of the present invention, a method for obtaining marker materials from a milk duct of a breast comprises locating a single milk duct, typically by labeling a ductal orifice present in the nipple of the breast. A washing fluid, typically saline, is introduced into the duct so that it passes substantially throughout the entirely ductal network, preferably without rupturing the duct. At least a portion of the washing fluid is then collected from the duct, and marker materials which may be present in the collected fluid (including fluids which might otherwise be secreted) are identified. While in some cases it may be desirable to collect specimens from only a single ductal network, it will usually be preferred to repeat the steps in order to identify the presence of marker materials in each of the ductal networks present in the breast. Cellular marker materials may comprise epithelial cells from the lining of the duct while the fluids will comprise normally secreted and non-secreted fluids present in the ducts. The epithelial and other cells obtained by the method will usually be morphologically histochemically, and/or immunohistochemically examined to determine if they are abnormal and to assess the likelihood of a cancer or pre-cancerous condition present in the cellular lining of the duct. Non-cellular marker materials include proteins, peptides, and other chemical species which may be secreted or otherwise released into a duct in response to a disease or other condition to be identified.

In a further aspect of the present invention, a preferred method for obtaining marker materials from a milk duct of a breast comprises locating at least one of the ductal orifices on the breast nipple. A dual-lumen catheter is then introduced through the orifice and into the ductal passage, usually over a guidewire. A washing fluid is then introduced through one of the lumens into the duct. Sufficient fluid is introduced so that the fluid will substantially fill the ductal volume and will then pass outwardly through the other of the catheter lumens so that it may be collected externally to the breast. Marker materials, such as epithelial and other cells, present in the collected washing fluid may then be isolated, detected and/or examined, as generally described above. Additionally, the ductal fluids present in the ducts prior to introduction of the washing fluid will be diluted and collected and may be examined for the presence of both small molecules and macromolecules, including proteins, carbohydrates, and other potential disease markers.

The volume of washing fluid introduced into the ductal network will usually be at least 5 ml, preferably being from 5 ml to 25 ml, usually being about 10 ml. The washing fluid will typically be introduced through the catheter lumen using a syringe at a generally low pressure which will not result in rupture of the ductal network. The washing fluid will be introduced over a relatively short time period, typically from 1 minute to 5 minutes, and will continue to be introduced even after the initial portions of the fluid begin to emerge from the second catheter lumen. As before, the method will usually be repeated for each of the ductal networks present in the breast.

According to yet a further aspect of the present invention, a kit for obtaining marker materials from a breast duct comprises a dual-lumen catheter together with instructions setting forth a method for use as described above. The kit will usually further comprise a package, such as a pouch, tray, tube, box, or the like. The instructions for use may be printed on a separate piece of paper, or optionally may be printed in whole or in part on a portion of the packaging. Usually, the dual-lumen catheter will be sterilized and maintained in a sterile condition within the packaging. Optionally, other system components, such as guidewires, saline or other washing fluid(s), cell growth and maintenance media, cell fixation media, cell collection trays, or the like, could be provided as part of the kit.

DESCRIPTION OF THE SPECIFIC EMBODIMENTS

Figure 1:
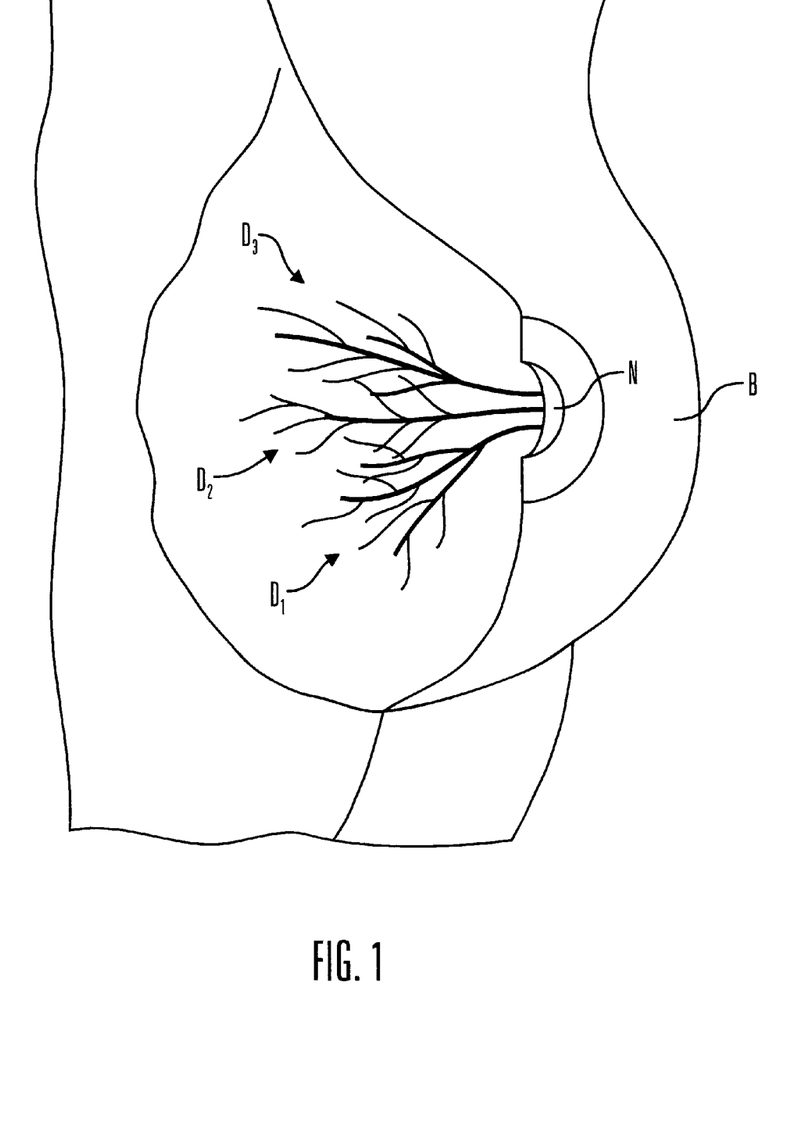
FIG. 1 is an anterior view of a human female breast, shown in section, and illustrating three of the six to nine ductal networks extending inwardly from the nipple.
Figure 2:
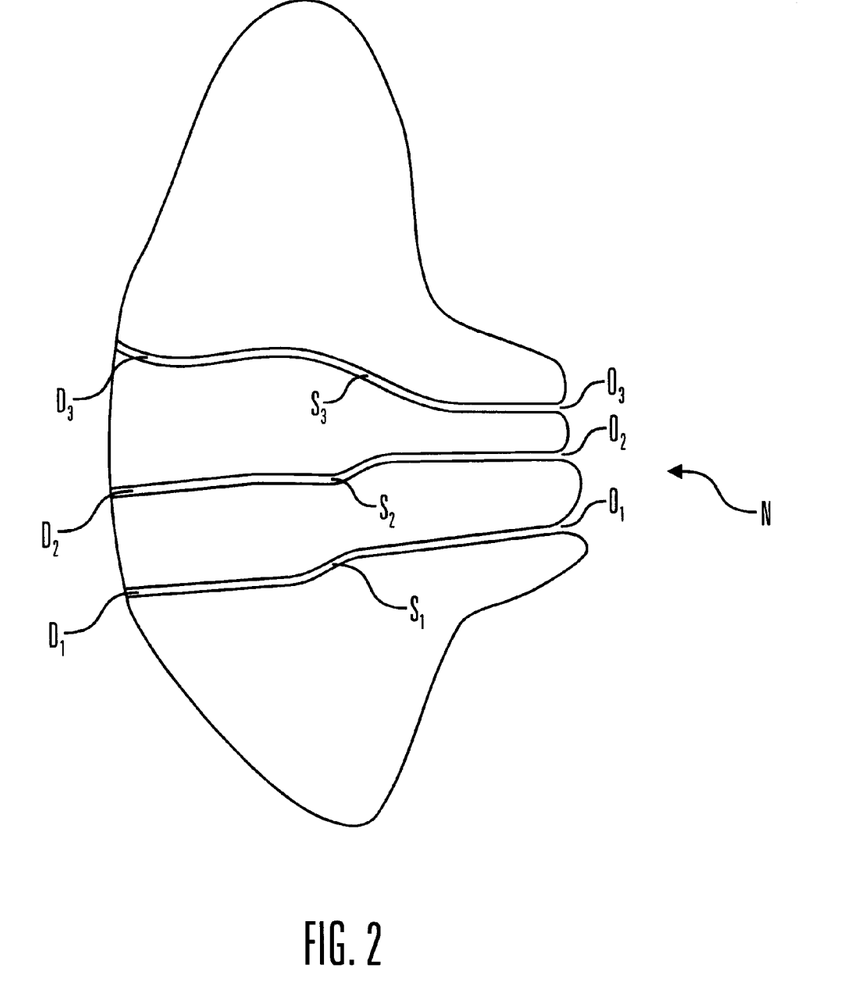
FIG. 2 is an enlarged view of the nipple of FIG. 1 illustrating the orifices leading to each of the three ductal networks.

The present invention comprises methods and kits for obtaining marker materials from one or more ductal networks in a human female breast. A typical breast B, as illustrated in FIG. 1, includes a nipple N and from six to nine ducts D. Three ductal networks $D_{1-3}$ extending inwardly from the nipple N into the breast tissue are illustrated. As best seen in FIG. 2, each ductal network $D_{1-3}$ begins with an orifice $O_{1-3}$ which lies at the surface of the nipple N and extends inwardly through a ductal sinus $S_{1-3}$ and then into a branching network. Each network D comprises a series of successively smaller lumens which are arranged in complex, three-dimensional patterns. The networks of each duct will overlap within the breast tissue but will not be interconnected. The total volume of each network is usually in the range from 0.1 ml to 0.5 ml, but the walls are somewhat compliant so the internal volume may increase as fluid is introduced. The present invention relies on accessing the ductal network(s) through the orifice O of the duct D within the nipple N. Usually, there will be from six to nine orifices which open into a like number of ductal networks. Confirmation of the number and location of the ductal orifices can be made by labelling the nipple as described below.

The present invention relies on collecting endogenous ductal fluids and cellular and non-cellular marker materials from the individual ductal networks on a duct-by-duct basis. That is, fluids and marker materials are obtained from a single duct without obtaining material from any other ducts. This is in contrast to prior techniques which, in some instances, are able to obtain cellular and other materials from all milk ducts at once by applying a mild vacuum to the nipple. It should be noted, however, that in some instances such screening of all ducts in a single step may be appropriate in order to identify patients showing abnormalities for whom further, duct-specific testing according to the present invention is appropriate.

As a first step of the method herein, a location of at least one duct will be determined, typically by labeling all ductal orifices as described in co-pending application Ser. No. 08/931,786, the full disclosure of which has previously been incorporated herein by reference. Briefly, a portion of the epithelial lining present exposed at the ductal orifice may be labeled with a visible marker which allows the treating professional to identify the entry orifice for each of the ductal networks in the breast. Following identification of the ductal orifice, a washing fluid will be introduced into the duct in order to loosen and mobilize cellular material from the ductal lining, primarily epithelial cells from the lining. The washing fluid is introduced in an amount and a manner such that substantially the entire volume of the duct will be washed with the fluid in order to obtain a sample which is representative of the entire ductal network. Cellular components from the sample will usually be of the most interest, but ductal fluids and secreted molecular species (both small molecules and more usually biological macromolecules such as proteins and carbohydrates) may also be analyzed. The washing fluid carrying the cells and other materials is then collected, and the materials morphologically, histologically, immunohistologically, chemically, immunologically, enzymatically, or otherwise examined in order to determine any abnormal or disease conditions within the ductal network, particularly cancer or a precancerous condition.

In the preferred embodiment, the washing fluid is introduced using a dual-lumen catheter which permits simultaneous introduction of the washing fluid and collection of excess washing fluid as it flushes back outwardly from the ductal network. The fluid being collected is usually not aspirated (since aspiration could collapse the duct), and instead the pressure of the introduced fluid is relied on to both flush the entire ductal network and expel the excess fluid through the other lumen of the cannula. Optionally, external pressure may be applied to the breast to enhance or expedite fluid collection. Typically, the fluid is introduced using a syringe, with the fluid being introduced at a relatively low rate, typically in the range from 0.1 ml/sec to 5 ml/sec, preferably from 0.5 ml/sec to 1 ml/sec. The total introduced volume of the washing fluid is typically at least 5 ml, typically being in the range from 5 ml to 25 ml, usually being about 10 ml, and optionally being greater. A preferred washing fluid is physiologic saline but contrast media and other physiologically acceptable, sterile fluids may also be used. Also contemplated is a method for obtaining material from a milk duct in a breast of a patient, said method comprising locating at least one of the ductal orifices on a nipple of the breast, introducing a catheter having at least one lumen through one of the dutcal orifices and into the ductal passage, introducing a washing fluid through a lumen into the ductal passage, collecting the washing fluid from the ductal passage through a lumen of the catheter, and identifying materials present in the collected washing fluid.

Figure 3:
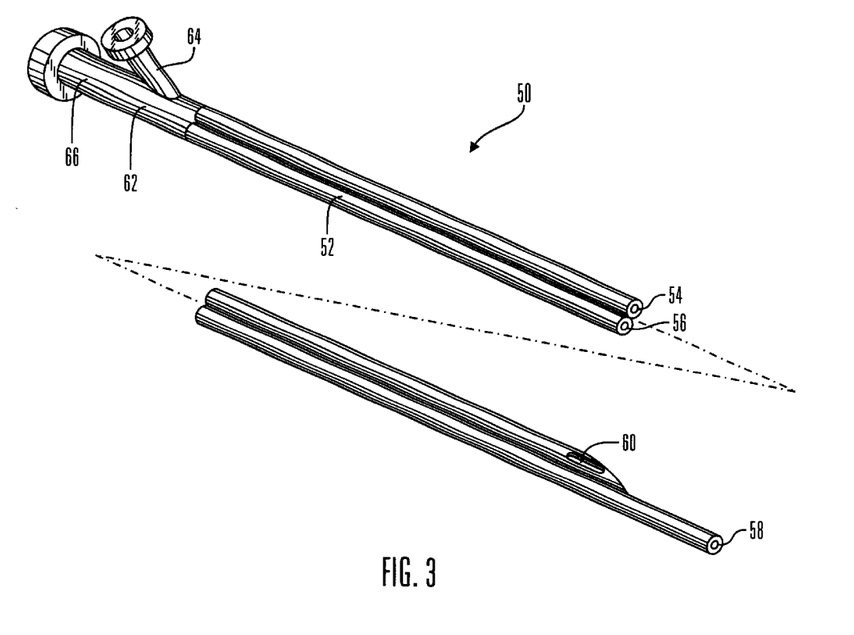
FIG. 3 is a perspective view of a dual-lumen catheter which is useful in performing the methods of the present invention.
Figure 4:
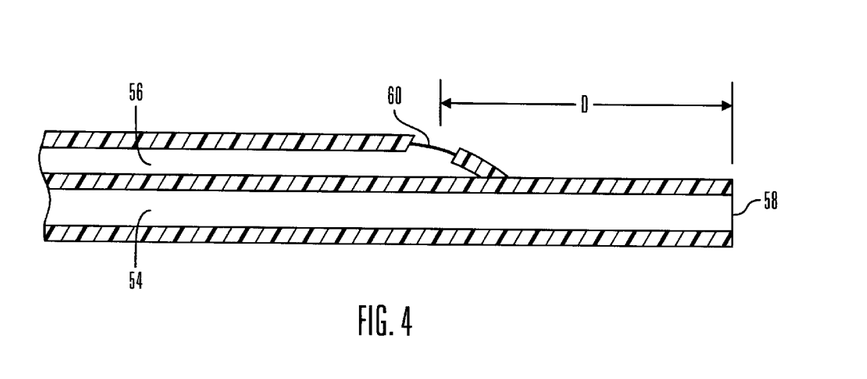
FIG. 4 is a detailed view of the distal end of the catheter of FIG. 3, shown in section.

An exemplary catheter 50 useful for performing the methods of the present invention is illustrated in FIGS. 3 and 4. The catheter comprises a catheter body 52, typically having a length in the range from 3 cm to 50 cm usually from 10 cm to 25 cm. The catheter body 52 includes at least a first lumen 54 and a second lumen 56. The first lumen 54 terminates in a distal port 58, as best seen in FIG. 4, while the second lumen terminates in a proximally located port 60, typically being located by a distance d which is approximately 0.1 cm to 1 cm, usually from 0.1 cm to 0.25 cm, proximal of the distal port 58. Catheter body 52 will have a relatively narrow diameter, typically having a maximum diameter in the dual-lumen region in the range from 0.8 mm to 2.5 mm, preferably being in the range from 0.8 mm to 1.2 mm. The diameter of the distal, single-lumen region may be less, as in the range from 0.5 mm to 1.5 mm, preferably from 0.6 mm to 1 mm. Proximal hub 62 includes a port 64 which is fluidly coupled to the second lumen 56 for delivering the washing fluid into the ductal network. Second port 66 is provided both for introducing the catheter over a guidewire and for collecting the washing fluid from the ductal network via port 58.

Figure 5:
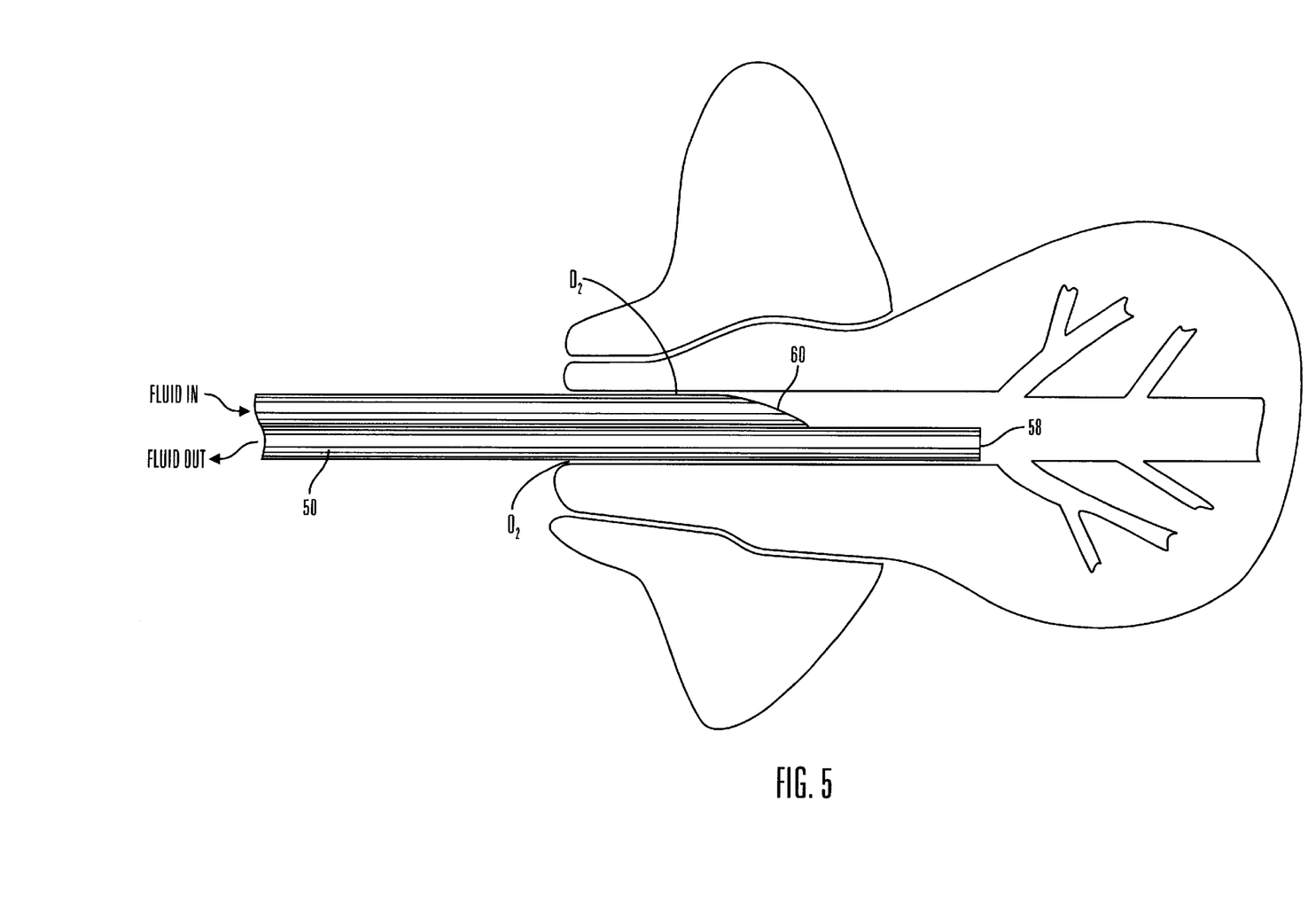
FIG. 5 illustrates use of the catheter of FIG. 3 in performing the method of the present invention in a single ductal network.

Referring to FIG. 5, use of the catheter 50 for collecting marker materials from a ductal network $D_2$ will be described. Usually, the ductal network $D_2$ will first be accessed with a guidewire, such as a conventional 0.014 inch guidewire (not shown). After the guidewire is introduced, typically by a distance in the range from 0.25 cm to 2.5 cm past the orifice $O_2$, the catheter 50 will be introduced over the guidewire by passing distal port 58 of the first lumen 54 over the external end of the guidewire. The distal port 58 is introduced into the ductal network $D_2$ typically to a depth of about 0.25 cm to 2.5 cm, usually about 0.75 cm to 1.5 cm. As discussed above, the second port 60 will be located proximally from the first port by a distance in the range from 0.1 cm to 1 cm, and will thus be closer to the orifice $O_2$. After the catheter 50 is in place, the guidewire will typically be withdrawn and the washing fluid introduced through the second lumen 56 via port 64 and opening 60. The washing fluid will flow into the ductal network and will generally reach most of the ductal volume, typically reaching at least 75% of the ductal volume, preferably at least 85%, and sometimes as much as 95%.

Alternatively, the guidewire and catheter 50 may be introduced simultaneously, typically with the distal tip of the guidewire extending a short distance ahead of the distal end of the catheter, usually about 0.1 cm to 1 cm. The guidewire is used to steer and the catheter 50 follows to the desired target location in the duct.

The volume of fluid introduced into the ductal network $D_2$ will be sufficiently large so that substantially the entire volume of the ductal network may be filled with the washing fluid and excess fluid will flow from the network as it is displaced by additional fluid input. Usually, only a small portion in the amount of washing fluid being introduced will be necessary to fill the ductal network, usually less than 1 ml, often less than 0.5 ml. The remaining fluid will continue to be introduced and will thus flush the cellular and other marker materials from the ductal network into the opening 58 in the first lumen 54. Thus, that fluid will pass outwardly through the catheter and may be collected from port 66 in the catheter. Preferably, no vacuum or other aspiration pressure will be applied to the catheter. Instead, the fluid will flow outwardly in response to the positive pressure created by the inflow of washing fluid, optionally with external pressure applied to the breast.

The collected fluid may be treated or analyzed in conventional ways to identify the presence, amount(s), identities, and/or other characteristics of any marker materials that may be present in the collected fluids. For example, cellular materials may be transferred to a suitable medium, such as RPMI or other growth or maintenance medium. The cells may then be examined morphologically under a microscope and/or histologically using suitable histochemical and immunochemical staining reagents. Chemical and molecular markers may be identified and/or examined chemically, immunologically, enzymatically, or by other conventional techniques. Such analysis techniques are well described in the art.

Figure 6:
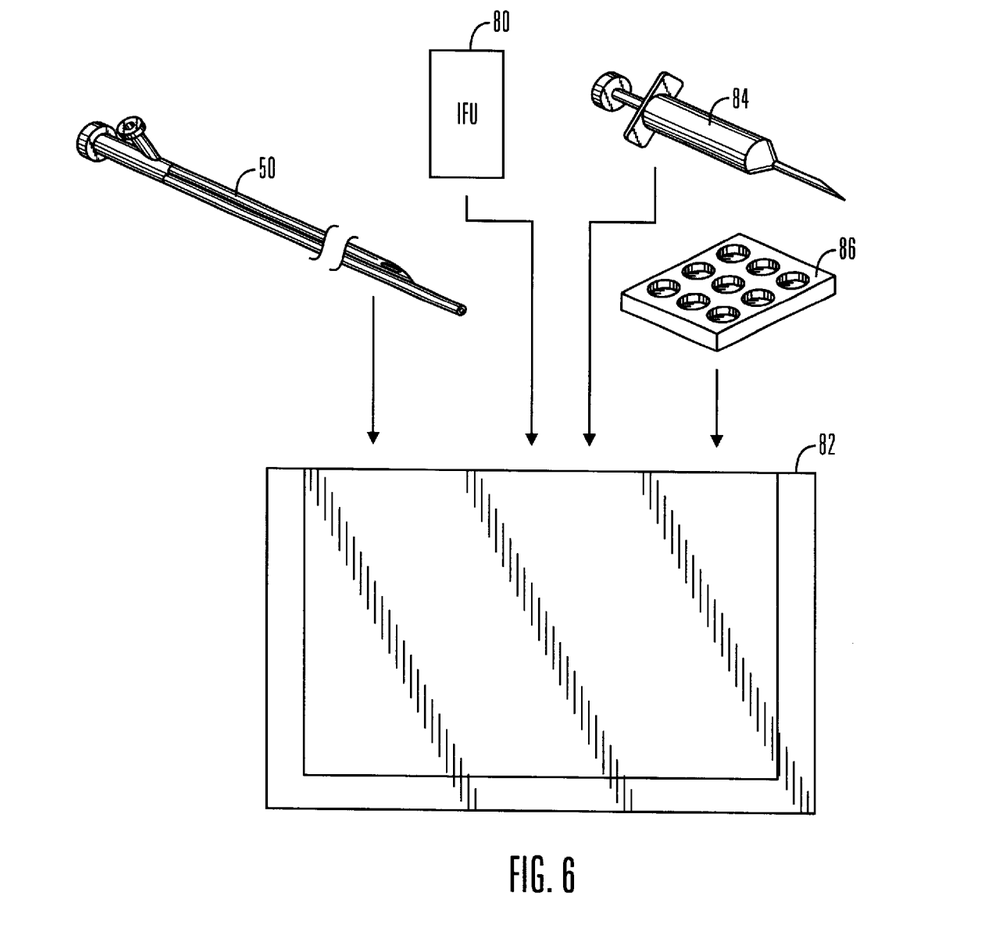
FIG. 6 illustrates a kit comprising a dual-lumen catheter and other system components, including instructions for use.

Kits according to the present invention will comprise at least a catheter 50 (which may be any dual- or multiple-lumen catheter capable of accessing an individual ductal network) and instructions for use (IFU) 80 which are combined together in a conventional manner, typically within a container 82, which may be in the form of a pouch, tray, box, tube, or the like. Kits will usually also include at least a guidewire, and other kit components may also be provided. For example, a syringe 84 may be provided, usually pre-filled with saline or other suitable washing medium for washing the ductal network. Additionally, a collection tray 86 for receiving and maintaining the cellular material and the washing fluids collected from the catheter may also be provided. Optionally, the tray may include a suitable collection medium, such as RPMI medium. Still further, the kits may include materials for assaying non-cellular markers as well as components for identification of the ductal orifice, such as described in co-pending application Ser. No. 08/931, 786, the full disclosure of which was previously incorporated herein by reference.

The following examples are offered by way of illustration, not by way of limitation.

EXPERIMENTAL

Figure 7A:
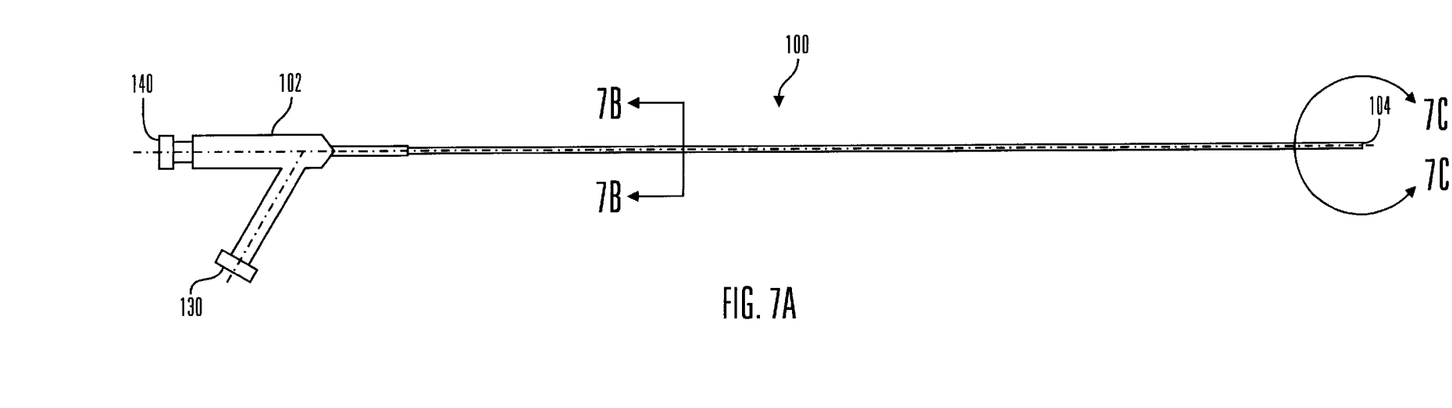
FIGS. 7A–7C illustrate the catheter utilized in the working examples hereinafter.
Figure 7B:
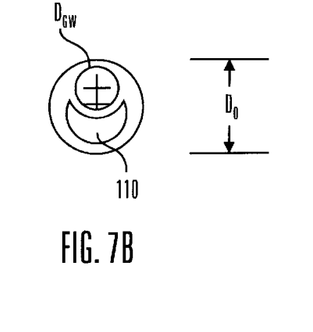
Figure 7C:
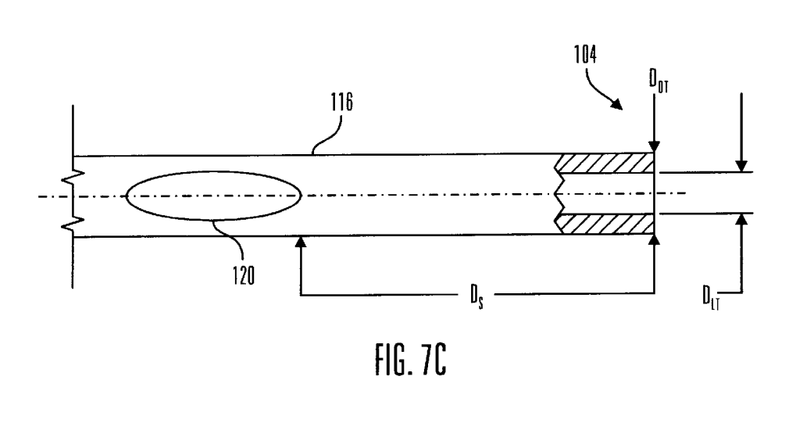

A double lumen catheter which would allow a continuous flow of saline throughout the ductal system was prepared, as illustrated in FIG. 7. The catheter was a 3 French double lumen catheter with the proximal lumen smaller in diameter and the distal larger to allow aspiration. In particular, the catheter 100 had a length from the hub 102 to the distal tip 104 of 31 cm, an outer diameter of $D_O$ of 0.041 in, a guidewire lumen $D_{GW}$ of 0.019 in, and a crescent-shaped lumen 110. The outer tip diameter $D_{OT}$ was 0.033 in and the lumenal tip diameter $D_{LT}$ was 0.017 in, reflecting a tapered distal end 116. A side port 120 having an oval geometry of 0.07 in×0.016 in formed the distal end of the lumen 110 and was spaced-proximally of the distal tip by a distance $D_S$ of 0.16 in. Fluid was introduced through port 130 and lumen 110 out through side port 120 into the ductal lumen. Fluid was collected through the distal tip and back through the guidewire lumen (after withdrawing the guidewire), and then through port 140. Initially the catheter was tested in breasts that had been removed surgically. Ten breasts were studied and cells were retrieved from seven. The catheter was also used with twelve anesthetized women prior to breast surgery. Cells were retrieved from ten of the twelve (83%). See Table 1.

Materials and Methods

After general anesthesia had been administered, the patient's breast was prepped and draped. Mild suction was applied to the nipple to try to elicit discharge. A dissecting microscope or loupe was used to magnify the nipple and identify orifices. A map was made of the identified orifices. Starting with the most promising orifice (i.e. most amount of discharge, and/or the largest), attempts were made to cannulate one or more orifices using either a standard set of metal dilators (galactography set by Mahan), or a very small guide wire of the type used in angiography. Once the duct had been cannulated and dilated to approximately 0.7–1.0 mm, the double lumen catheter was threaded into the duct. Saline was instilled, setting up a continuous flow until 10 cc was collected. The procedure took about 15 minutes. If 10 cc of fluid was not collected within the 15 minute limit, the procedure stopped prematurely. The washings were then sent to cytology for analysis.

Results

The results are show in Table 1.

TABLE 1

| patient # | breast | mass location | duct location | #duct | pathology | cytology |
|---|---|---|---|---|---|---|
| Detached breasts | | | | | | |
| 1 | R | RLQ | central | 1 | Ductal carcinoma comedo | acellular |
| 2 | R | No cancer | 6:00 | 3 | | ductal cells |
| | L | L breast | 9:00, 7:00 | 3 | Micro-papillary DCIS | ductal cells |
| 3 | L | LLQ | 12:00 | 3 | infiltrating ductal carcinoma | ductal cells |
| 4 | R | RUOQ | 8:00 | 4 | DCIS pagetoid | ductal cells |
| 5 | L | LUOQ | 11:00 | 5 | Intraductal carcinoma in situ | ductal cells |
| 6 | R | no cancer | 9:00 | 2 | | acelluar |
| | L | 3:00, 9:00 | 6:00 | 4 | Invasive ductal car-cinoma, DCIS | acelular |
| 7 | L | LUOQ | 6:00 | 4 | Infiltrating ductal car-cinoma, DCIS | (1) acellular, (2) ductal cells |
| 8 | L | LOQ, 3:00 | central | 2 | Infiltrating lobular car-cinoma, infiltrating ductal | ductal cells |
| Attached breasts | | | | | | |
| 1 | R | RUOQ | 12:00 | 2 | adeno ca | carcinoma cells |
| 2 | L | retro-aerolar | central | 1 | poorly diff. ductal carcinoma | deter-iorated cells |
| 3 | R | RUOQ | 3:00 | 3 | tubular car-cinoma, micro-papillary | deter-iorated cells |
| 4 | L | infra-aerolar | 9:00 | 2 | invasive ductal carcinoma | deter-iorated cells |

TABLE 1-continued

| patient # | breast | mass location | duct location | #duct | pathology | cytology |
|---|---|---|---|---|---|---|
| 5 | R | N/A (abscess) | central | 1 | lactiferous duct | Acellular |
| 6 | L | LUOQ | 3–4:00 | 1 | fiber-adenoma | Benign mammary epithelial cells |
| 7 | R | | 3:00 | | fi-broad enoma | A-bund epithelial cells, benign mammary epithelial cells |
| 8 | R | 12:00 | 12:00 | 2 | Invasive ductal carcinoma | Acellular, rare, ductal cells |
| 9 | R | 11:00 | 11:00 | 3 | Invasive lob-ular | acellular |
| 10 | L | UOQ | central | 1 | Invasive lobular | Mod macrophage, no ductal cells |
| 11 | L | LUOQ | central | 1 | Adeno carcinoma | Foam cells ductal cells |
| 12 | R | RUOQ | 3:00 | 2 | Atyp med carcinoma | Foam cells, rare ductal cells |

R: right
L: left
RLQ: right lower quadrant
LLQ: left lower quadrant
LUOQ: left upper outer quadrant
LOQ: left outer quadrant
RUOQ: right upper outer quadrant
UOQ: upper outer quadrant
DCIS: ductal carcinoma in situ While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of assessing the likelihood of a cancer in the cellular lining of a breast duct, said method comprising:
   (a) locating at least one of the ductal orifices on a nipple of the breast;
   (b) introducing a catheter having at least two lumens through one of the ductal orifices and into the ductal passage;
   (c) introducing a washing fluid through a lumen into the ductal passage;
   (d) collecting the washing fluid from the ductal passage through a lumen of the catheter while the catheter is within the ductal passage, wherein the material in the collected fluid include epithelial cells; and
   (e) examining the morphology of the epithelial cells in the collected fluid to determine if they are atypical in order to assess the likelihood of a cancer present in the cellular lining of the duct.

2. A method of assessing the likelihood of a cancer in the cellular lining of a breast duct, said method comprising:
   (a) locating all ductal orifices on a nipple of the breast;
   (b) introducing a catheter having at least two lumens through a first of the ductal orifices and into a first ductal network;
   (c) introducing a washing fluid through a lumen of the catheter into the ductal passage;
   (d) collecting the washing fluid from the ductal passage through a lumen of the catheter while the catheter is within the ductal passage, wherein the material in the collected fluid include epithelial cells;
   (e) repeating steps (b)–(d) for all other ductal networks, whereby material from each network can be identified separately; and
   (f) examining the morphology of the epithelial cells in the collected fluid to determine if they are atypical in order to assess the likelihood of a cancer present in the cellular lining of a duct.

3. A method of assessing the likelihood of a cancer in the cellular lining of a breast duct, said method comprising:
   (a) locating at least one of the ductal orifices on a nipple of the breast;
   (b) introducing a catheter having at least two lumens through one of the ductal orifices and into the ductal passage;
   (c) introducing at least 5 ml of a washing fluid through a lumen into the ductal passage;
   (d) collecting the washing fluid from the ductal passage through a lumen of the catheter while the catheter is within the ductal passage, wherein the material in the collected fluid include epithelial cells; and
   (e) examining the morphology of the epithelial cells in the collected fluid to determine if they are atypical in order to assess the likelihood of a cancer present in the cellular lining of the duct.

4. A method for identifying material in a milk duct in a breast of a patient, said method comprising:
   (a) locating at least one of the ductal orifices on a nipple of the breast;
   (b) introducing a catheter having at least one lumen two lumens through one of the ductal orifices and into the ductal passage;
   (c) introducing a washing fluid through a lumen into the ductal passage;
   (d) collecting the washing fluid from the ductal passage through a lumen of the catheter while the catheter is within the ductal passage; and
   (e) identifying materials present in the collected washing fluid.

5. A method for identifying material in a milk duct in a breast of a patient, said method comprising:
   (a) locating all ductal orifices on a nipple of the breast;
   (b) introducing a catheter having at least two lumens through a first of the ductal orifices and into a first ductal network;
   (c) introducing a washing fluid through a lumen of the catheter into the ductal passage;
   (d) collecting the washing fluid from the ductal passage through a lumen of the catheter while the catheter is within the ductal passage,
   (e) identifying materials present in the collected washing fluid collected from the first ductal network; and
   repeating steps (b)–(e) for all other ductal networks, whereby material from each network can be identified separately.

6. A method for identifying material in a milk duct in a breast of a patient, said method comprising:
   (a) locating at least one of the ductal orifices on a nipple of the breast;
   (b) introducing a catheter having at least two lumens through one of the ductal orifices and into the ductal passage;
   (c) introducing at least 5 ml of a washing fluid through a lumen into the ductal passage;
   (d) collecting the washing fluid from the ductal passage through a lumen of the catheter while the catheter is within the ductal passage; and
   (e) identifying materials present in the collected washing fluid.

7. A method for collecting material from a milk duct in a breast of a patient, said method comprising:
   (a) locating at least one of the ductal orifices on a nipple of the breast;
   (b) introducing a catheter having at least two lumens through one of the ductal orifices and into the ductal passage;
   (c) introducing a washing fluid through a lumen into the ductal passage; and
   (d) collecting the washing fluid from the ductal passage through a lumen of the catheter while the catheter is within the ductal passage.

8. A method as in claim 7, further comprising dilating the ductal orifice prior to introducing the catheter.

9. A method as in claim 7, wherein the washing fluid introducing and collecting steps are performed through separate lumens in the catheter.

10. A method as in claim 9, wherein a preselected volume of the washing fluid is introduced to the duct through one lumen and excess volume flows out of the duct through another catheter lumen.

11. A method as in claim 10, wherein the volume of washing fluid is at least 5 ml.

12. A method as in claim 8, wherein the volume of washing fluid is at least 10 ml.

13. A method as in claim 7, further comprising collecting material from at least one additional single milk duct of the same breast by repeating steps (a) through (d) on another single milk duct.

14. A method as in claim 13, wherein the steps are repeated for all ducts in the nipple.

15. A method as in claim 7, wherein the material in the washing fluid include epithelial cells.

16. A method as in claim 7, wherein the materials comprise non-cellular species.

17. A method for collecting material from a milk duct in a breast of a patient, said method comprising:
   (a) locating all ductal orifices on a nipple of the breast;
   (b) introducing a catheter having at least two lumens through a first of the ductal orifices and into a first ductal network;
   (c) introducing a washing fluid through a lumen of the catheter into the ductal passage;
   (d) collecting the washing fluid from the ductal passage through a lumen of the catheter while the catheter is within the ductal passage; and
   repeating steps (b)–(d) for all other ductal networks, whereby material from each network can be collected separately.

18. A method as in claim 17, further comprising dilating the ductal orifice prior to introducing the catheter.

19. A method as in claim 17, wherein the washing fluid introducing and collecting steps are performed through separate lumens in the catheter.

20. A method as in claim 19, wherein a preselected volume of the washing fluid is introduced to the duct through one lumen and excess volume flows out of the duct through another catheter lumen.

21. A method as in claim 20, wherein the volume of washing fluid is at least 5 ml.

22. A method as in claim 20, wherein the volume of washing fluid is at least 10 ml.

23. A method as in claim 17, wherein the material in the washing fluid includes epithelial cells.

24. A method as in claim 17, wherein the material in the washing fluid comprises non-cellular species.

25. A method for collecting material from a milk duct in a breast of a patient, said method comprising:
   (a) locating at least one of the ductal orifices on a nipple of the breast;
   (b) introducing a catheter having at least two lumens through one of the ductal orifices and into the ductal passage;
   (c) introducing at least 5 ml of a washing fluid through a lumen into the ductal passage; and
   (d) collecting the washing fluid from the ductal passage through a lumen of the catheter while the catheter is within the ductal passage.

26. A method as in claim 25, further comprising dilating the ductal orifice prior to introducing the catheter.

27. A method as in claim 25, wherein the washing fluid introducing and collecting steps are performed through separate lumens in the catheter.

28. A method as in claim 27, wherein the washing fluid is introduced to the duct through one lumen and excess volume flows out of the duct through another catheter lumen.

29. A method as in claim 25, wherein the volume of washing fluid is at least 10 ml.

30. A method as in claim 25, further comprising collecting material from at least one additional single milk duct of the same breast by repeating steps (a) through (d) on another single milk duct.

31. A method as in claim 30, wherein the steps are repeated for all ducts in the nipple.

32. A method as in claim 25, wherein the material in the washing fluid include epithelial cells.

33. A method as in claim 25, wherein the materials comprise non-cellular species.

* * * * *

UNITED STATES PATENT AND TRADEMARK OFFICE
Certificate

Patent No. 6,221,622 B1                                                                     Patented: April 24, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Susan M. Love, Pacific Palisades, CA; and Sanford H. Barsky, Los Angeles, CA.

Signed and Sealed this Twenty-fifth Day of March 2003.

ANTHONY CAPUTA
*Supervisory Patent Examiner*
Art Unit 1642

UNITED STATES PATENT AND TRADEMARK OFFICE
CERTIFICATE OF CORRECTION

PATENT NO.    : 6,221,622 B1
DATED         : April 24, 2001
INVENTOR(S)   : Susan M. Love and Sanford H. Barsky It is certified that error appears in the above-identified patent and that said Letters Patent is hereby corrected as shown below:

Column 10,
Line 41, after "least" strike "one lumen".

Signed and Sealed this

Eighth Day of March, 2005

JON W. DUDAS
*Director of the United States Patent and Trademark Office*